US006960687B2

(12) United States Patent
Bialer et al.

(10) Patent No.: US 6,960,687 B2
(45) Date of Patent: Nov. 1, 2005

(54) DERIVATIVES AND PHARMACEUTICAL COMPOSITIONS OF N-HYDROXYALKYL TETRAMETHYLCYCLOPROPANE-CARBOXAMIDE, HAVING ANTI-EPILETIC, NEUROLOGICAL, AND CNS ACTIVITY, AND METHOD FOR THEIR PREPARATION

(75) Inventors: Meir Bialer, Jerusalem (IL); Nina Isoherranen, Seattle, WA (US); Boris Yagen, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/503,235

(22) PCT Filed: Dec. 29, 2002

(86) PCT No.: PCT/IL02/01050

§ 371 (c)(1),
(2), (4) Date: Feb. 24, 2005

(87) PCT Pub. No.: WO03/064374

PCT Pub. Date: Aug. 7, 2003

(65) Prior Publication Data

US 2005/0131069 A1 Jun. 16, 2005

(30) Foreign Application Priority Data

Feb. 1, 2002 (IL) ...................................... 147953

(51) Int. Cl.$^7$ .................... C07C 233/58; A61K 31/165
(52) U.S. Cl. ...................................... 564/190; 514/624
(58) Field of Search ........................ 564/190; 514/624

(56) References Cited

U.S. PATENT DOCUMENTS

| 5,880,157 | A  | 3/1999  | Sterling et al. |
| 6,417,399 | B1 | 7/2002  | Bialer et al. |
| 6,630,602 | B1 | 10/2003 | Bialer et al. |
| 2002/0115718 | A1 | 8/2002 | Chen et al. |

FOREIGN PATENT DOCUMENTS

| WO | WO 95/09835 | 4/1995 |
| WO | WO 95/21814 | 8/1995 |
| WO | WO 98/30538 | 7/1998 |
| WO | WO 99/48859 A | 9/1999 |
| WO | WO 99/54282 | 10/1999 |
| WO | WO 02/46188 A | 8/2002 |

OTHER PUBLICATIONS

Bialer, Meir et al "Pharmacokinetic Analysis and Antiepileptic Activity of Tetra-Methylcyclopropane Analogues of Valpromide" Pharmaceutical Research (1996) vol. 13, No. 2, pp: 284-189.

Bialer M "Pharmacokinetic considerations in the design of better and safer new antiepileptic drugs" Journal of Controlled Release, Elsevier Science Publishers B.V. Amsterdam, NL, (Nov. 1, 1999) vol. 62, co. 1-2 pp:187-192.
Bialer M et al "Pharmacokinetics of a Valpromide Isomer. Valnoctamide, in Healthy Subjects" European Journal of Clinical Pharmacology, Springer Verlag, DE (1990) vol. 38, No. 3. pp:289-291, XP002063380 ISSN: 0031-6970 ★p. 289★.
Database BIOSIS 'Online!' Biosciences Information Service, retrieved from MEDLINE Database accession No. prev199698701231 XP002235669 abstract & Bialer Meir et al "Pharmacocinetic analysis and antiepileptic activity of tetra-methylcyclopropane analogues of valpromide" Pharmaceutical Research (1996) vol. 13, No. 2, pp: 284-289.
Database BIOSIS 'Online!' Biosciences Information Service, retrieved from MEDLINE Database accession No. prev199799414598 XP002235672 abstract Malhotra Jatinder et al "Effect of adenosine receptor modulation on pentylenetetrazole—induced seizures in rates" British Journal of Pharmacology (1997) vol. 120, No. 2, pp. 282-288.
Database BIOSIS 'Online!' Biosciences Information Service, retrieved from MEDLINE Database accession No. prev199800261866 XP002235673 abstract & Blotnik Simcha et al"Disposition of two tetramethylcyclopropane analogues of valpromide in the brain, liver, plasma and urine of rats" European Journal of Pharmaceutical Sciences (1998) vol. 6, No. 2, pp: 93-98.
Database BIOSIS 'Online!' Biosciences Information Service, retrieved from MEDLINE Database accession No. prev200200550317 XP002235671 abstract & Huber Alexander, Guttinger Martin et al: "Seizure suppression by adenosine A2A receptor activation in a rat model of audiogenic brainstem epilepsy" Neuroscience Letters, vol. 329, No. 3, (Sep. 6, 2002) pp:289-292.
Database BIOSIS 'Online!' Chemical Abstracts Service, retrieved from Registry Database accession No. 1975:478893 XP002235674 abstract & ZA 7 400 202 A (Hexachimie S.A., FR) (Nov. 27, 1974.
Greenberg M.L. et al "Inhibition of myo-inositol-phosphate synthase by valproate: a mechanism for mood stabilization "European Neuropsychopharmacology (2003) vol. 13 (Supplement 4) pp: S107-S108.

(Continued)

Primary Examiner—Shailendra Kumar
(74) Attorney, Agent, or Firm—Browdy and Neimark, PLLC

(57) ABSTRACT

New derivatives of N-Hydroxyalkyl-tetramethylcyclopropane carboxamide, pharmaceutical compositions thereof, methods for their preparation, and use thereof for the treatment of epilepsy, neurological, affective and psychotic disorders and for the treatment of pain and migraine.

8 Claims, No Drawings

OTHER PUBLICATIONS

Isoherranen Nina et al "Anticonvulsant profile and teratogenicity of N-methylcyclopropyl carboxamide: A new antiepileptic drug" Epilepsia (2002) vol. 43, No. 2, pp: 115-126.

Isoherranen Nina et al "New CNS-active drugs which are second-generation valproic acid: can they lead to the development of a magic bullet?" Current Opinion in Neurology (2003) vol. 16, pp:203-211.

Jinming Gao et al "Increasing Binding Constants of Ligands to Carbonic Anhydrase by Using Greasy Tails" J. Med. Chem. (1995) vol. 38, pp:2292-2301.

Shamir Agam G. et al "Myo-inositol-1-phosphate (MIP) synthase: a possible new target for antibipolar drugs" Bipolar Disorders (2002) vol. 4 (Supple. 1) pp:15-20.

Shuto S et al "Synthesis and Biological Activity of Conformationally Restricted Analogs of Milnacipran:(1S, 2R)-1-Phenyl-2-U(S)-1-Aminopropyl)-N,N-DI Ethylcyclopropanecarboxamide, and Efficient Noncompetitive N-Methyl-D-Aspartic Acid Recepto Antagonist" Journal of Medicinal Chemistry, American Chemical Society (Nov. 22, 1996) vol. 39, No. 24, pp:4844-4852.

Shuto S et al "(Plus or Minus)-(Z)-2-(Aminomethyl)-1-Phenylcyclopropanecarboximide Derivatives as a New Prototype of NMDA Receptor Antagonists" Journal of Medicinal Chemistry, American Chemical Society (Jul. 21, 1995) vol. 38, No. 15, pp:2964-2968.

Spiegelstein O et al "Enantioselective Synthesis and Teratogenicity of Propylisopropyl Acetamide, a CNS-Active Chiral Amide Analogue of Valproic Acid" Chirality (1999) vol. 1, pp:645-650.

DERIVATIVES AND PHARMACEUTICAL COMPOSITIONS OF N-HYDROXYALKYL TETRAMETHYLCYCLOPROPANE-CARBOXAMIDE, HAVING ANTI-EPILETIC, NEUROLOGICAL, AND CNS ACTIVITY, AND METHOD FOR THEIR PREPARATION

This application is a 371 of PCT/IL02/01050, filed Dec. 29, 2002.

FIELD OF THE INVENTION

The invention relates to new derivatives of tetramethylcyclopropane carboxylic acid, an analog of Valproic acid, methods for their preparation, and use thereof for the treatment of epilepsy, neurological, affective and psychotic disorders and for the treatment of pain and migraine.

BACKGROUND OF THE INVENTION

Four major antiepileptic drugs (AEDs) are used for the treatment of epilepsy (epileptic seizures and convulsions): phenytoin, carbamazepine, phenobarbital and valproic acid (VPA). However, about 25% of the patients do not respond to the current medications. Furthermore, AEDs are administered repetitively as chronic treatment and the adverse effects associated with antiepileptic therapy are of a major concern. All the established AEDs are associated with some rare but severe side effects such as teratogenicity. In addition, all the AEDs have other adverse effects that limit their use. Valproic acid itself has considerable adverse effects including fatal hepatotoxicity.

One approach to obtain improved antiepileptic agents has been to prepare the primary amide derivatives of valproic acid and its analogs. Valnoctamide (VCD) and propylisoproylacetamide (PID) are amide derivatives of valproic acid that have improved anticonvulsant activity when compared to VPA. These amide analogues of valproic acid have been shown to be non-teratogenic, O. Spiegelstein, M. Bialer, M. Radatz, H. Nau and B. Yagen Chirality, 11:645–650 (1999).

Amide derivatives of Tetramethylcyclopropane carboxylic acid have also been previously evaluated for their anticonvulsant activity (M. Bialer, S. Hadad, B. Kadry, A. Abdul-Hai, A. Haj-Yehia, J. Sterling, Y Herzig and B. Yagen Pharm Res. 13:284–289 (1996)). These derivatives had good anticonvulsant activity (J. Sterling, et al. U.S. Pat. No. 5,880,157, issued March. 1999) and superior brain penetration than VPA. The N-Methyl-tetramethylcyclopropane carboxamide has a wide spectrum of anticonvulsant activity and is approximately 10 times more potent than VPA in animal models of epilepsy. In addition, N-Methyl-tetramethylcyclopropane carboxamide and Tetramethylcyclopropane carboxamide were not teratogenic in mouse model of antiepileptic drug induced teratogenicity.

Based on the success of VPA and VCD in treatment of nonepileptic disorders it is expected that an amide derivative of VPA will be effective in migraine, neuropathic pain and mania (bipolar disorders).

SUMMARY OF THE INVENTION

The present invention relates to a compound having the formula (I):

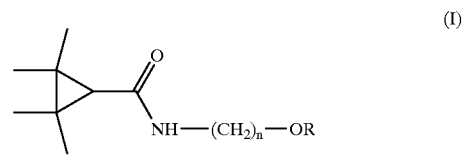

wherein n=1–6 and wherein R is hydrogen, an alkyl group of 1–3 carbons, an arylalkyl group, an aryl group, a carboxamide or N-Methyl or N-dimethyl carboxamide, especially useful for the treatment of affective illness, cognitive disorders, neurodegenerative diseases, neuropathic pain, migraines, epilepsy, stroke, brain ischema, and head trauma injury.

The present invention also relates to a pharmaceutical composition, comprising an effective amount of compound (I) as an active ingredient and any pharmaceutically acceptable carrier or diluent.

DESCRIPTION OF THE INVENTION

The present invention relates to compounds of particularly high activity and low toxicity that result from the coupling of tetramethylcyclopropane carboxylic acid with hydroxymethylamine or ethanolamine and having the formula (I) shown above.

Preferably n of formula (I) is an integer from 1 to 6, more preferably from 1 to 4 and most preferably n=1 or 2.

In preferred embodiments, examples of the compound according to the invention include:
N-Hydroxymethyl-tetramethylcyclopropane carboxamide;
N-Hydroxyethyl-tetramethylcyclopropane carboxamide;
N-Methoxymethyl-tetramethylcyclopropane carboxamide;
N-Ethoxymethyl-tetramethylcyclopropane carboxamide;
N-Propoxymethyl-tetramethylcyclopropane carboxamide;
N-Benzoxymethyl-tetramethylcyclopropane carboxamide;
N-Methoxyethyl-tetramethylcyclopropane carboxamide;
N-Ethoxyethyl-tetramethylcyclopropane carboxamide;
N-Propoxyethyl-tetramethylcyclopropane carboxamide;
N-Benzoxyethyl-tetramethylcyclopropane carboxamide;

The invention further provides a pharmaceutical composition comprising any compound hereinabove named in a therapeutically effective amount and a pharmaceutically acceptable carrier. Preferably, the therapeutically effective amount is an amount from about 10 to about 500 mg. Moreover, according to certain preferred embodiments of the present invention, the carrier is preferably a solid and the composition is a tablet. Alternatively, according to other preferred embodiments of the present invention, the carrier is selected from the group consisting of an oil, a fat, a wax, a synthetic triglyceride, a polymer and mixtures thereof and the composition is a suppository. According to yet other preferred embodiments of the present invention, the carrier is a liquid and the composition is a solution.

The present invention also related to a method for treating epilepsy, affective illness, cognitive disorders, neurogenerative disease, neuropathic pain syndrome, migraine, stroke, brain ischemia, and head trauma injury, comprising administering to subject an effective amount of the compound of formula (I).

The compounds of formula (I) are potent anticonvulsant agents in conventional models of human epilepsy. Several of the compounds have a surprisingly better therapeutic profile than valproic acid. Furthermore, they may also be useful in treatment of other CNS dysfunction. The compounds of the invention are highly effective in the scMet (subcutaneous Metrazole) test. The median effective doses ($ED_{50}$) of the agents claimed herein are considerably lower than those required to produce neurological impairment. Therefore, results in animal models distinguish the compounds of the present invention from other antiepileptic agents and indicate that the disclosed compound is effective against generalized and partial seizures, in addition to other forms of epilepsy.

Reference will now be made to the first set of reactions shown in diagram below. The compounds of formula (I) with n=1 may be prepared via conventional amidation processes, e.g., by reacting an activated form (acyl chloride) of the tetramethyl cyclopropane carboxylic acid with ammonia, then further reacting the obtained amide with formaldehyde in presence of a basic catalyst. The basic substance employed for the purpose is an alkali, such as trimethylamine, or triethylamine and must be present in a quantity sufficient to catalyze the reaction. The product here obtained is then (optionally) further reacted with an alkyliodide or aryliodide in order to obtain Compound (IV).

Compound (I) may be prepared from Compound (II) by reacting Compound (II) with Formaldehyde in an inert water-miscible organic solvent, e.g. tetrahydrofuran, at a temperature ranging between 25° and 70° C., preferably at 50°–60° C., for a period of 1 to 24 hrs, preferably 10 to 14 hrs. The resulting hydroxymethylamide may be isolated and purified.

Referring to the second set of reactions shown in the diagram, the compounds of formula (I) with n=2 may be prepared via conventional amidation processes, e.g., by reacting an activated form (acyl chloride) of the tetramethyl cyclopropane carboxylic acid with ethanolamine to obtain Compound (V). The product here obtained is then further reacted with an alkyliodide or aryliodide in order to obtain Compound (VI).

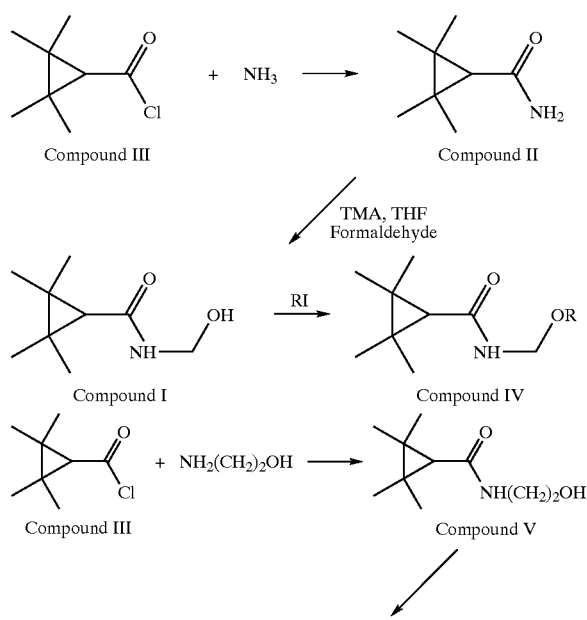

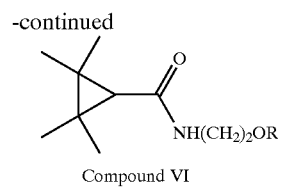

Compound VI

The reaction of Compound (III) with ammonia or ethanolamine may be carried out in an aqueous solution of the amine or in a halogenated organic solvent, such as chloroform or dichloromethane and has been previously described in U.S. Pat. No. 5,880,157.

In the practice of the invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier, and route of administration being employed and the frequency with which the composition is to be administered. A pharmaceutical composition in unit dose form for treatment of the disorders listed hereinabove preferably comprises 10 to 500 mg of the active ingredient.

In a preferred embodiment, the compound is administered in a pharmaceutical composition which comprises the compound and a pharmaceutically active carrier. As used herein, the term "pharmaceutically acceptable carrier" encompasses any of the standard pharmaceutically accepted carriers, such as a phosphate buffered saline solution, water, emulsions such as oil/water emulsion or a triglyceride emulsion, various types of wetting agents, tablets, coated tablets and capsules. An example of an acceptable triglyceride emulsion useful in the intravenous and intraperitoneal administration of the compounds is the triglyceride emulsion commercially distributed under the tradename Intralipid.

Typically, such carriers contain excipients such as starch, milk, sugar, certain types of clay, gelatin, stearic acid, talc, vegetable fats and oils, gums, glycols, or other known excipients. Such carriers may also include flavor and color additives or ingredients.

In the practice of the invention, the administration of the pharmaceutical composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments, or transdermal patches.

The following Experimental Details are set forth to aid in an understanding of the invention, are not intended, and should not be construed, to limit in any way the invention set forth in the claims that follow thereafter.

EXAMPLE 1

Tetramethyl-cyclopropane-carbonylchloride (15 g, 0.093 mol) was added dropwise to a 25% aqueous solution of ammonia (100 mL) at ambient temperature. The two-phase mixture was stirred at RT overnight. 100 mL of water was then added and the aqueous layer extracted with DCM (2*200 mL). The combined organic layers were washed successfully with carbonate buffer, dried and evaporated to dryness. The residue was treated with chloroform:hexane (100 ml), and the resultant chrystals were collected by filtration washed with hexane and dried to give 10 g (0.071 mol, 76%) of the title compound as a white solid, mp 90° C.

EXAMPLE 2

4 g, 0.028 mol of Tetramethyl-cyclopropane-carboxamide (compound II) prepared according to Example 1 was added to a solution of Trimethylamine (20 mL) and formaldehyde (20 mL) in tetrahydrofurane (100 ml). The reaction mixture was stirred in 60° C. for 12 hours. The excess of THF and formaldehyde was then distilled using reduced pressure and the residue containing the product N-hydroxymethyl-tetramethylcyclopropane-carboxamide (compound I) treated with $CHCl_3$. The resultant crystals were collected by filtration washed with hexane and dried to give 3 g (0.175 mol, 63%) of the title compound as a white solid, mp 135° C.

EXAMPLE 3

Biological Activity

Compound I (of the above diagram) was screened for its ability to protect against chemically and electrically induced convulsions, in three models of epilepsy in rodents. The first model, the maximal electroshock seizure test (MES), is used to show efficacy for antiepileptic agents against partial and generalized seizure type epilepsy, the common epilepsy among therapy resistant epileptic patients. The second model, the subcutaneous metrazole test (sc Met) measures seizure threshold and is a standard screening procedure to show efficacy for agents against seizure threshold and absence seizures. The third model is the 6 Hz psychomotor seizure model, a model that screens for focal seizures and has been used to find new antiepileptic compounds with novel mechanisms of action. In these studies, convulsions were inhibited or prevented in mice following imtraperitoneal (ip) administration of compound 1.

N-Hydroxymethyl-tetramethylcyclopropane-carboxamide (compound I) showed anticonvulsant activity in mice in the MES test. The $ED_{50}$ (mice ip) in the MES model is between 150 and 300 mg/kg in mice (Table 1). This value is slightly lower than that of VPA in mice. The results are indicative of the compound 1 having an efficacy against generalized seizures and complex partial seizures that evolve into generalized motor seizures.

Compound I showed anticonvulsant activity in mice in the scMet test. The $ED_{50}$ (mice) in the scMet model is 120 mg/kg in mice (Table 1). This value is slightly lower (more efficacious) than that found for VPA in mice. The results are indicative of the compound 1 having an efficacy against absence seizures and ability to raise seizure threshold.

Compound 1 was also efficacious in the 6 Hz model of psychomotor seizures in mice. The $ED_{50}$ in the 6 Hz model at stimulation intensity of 32 mA was 91 and on stimulation intensity of 44 mA it was 134 mg/kg. Compound 1 is 1.38 times more active compared to VPA in the 6 Hz 32 mA test and 2.31 times more active compared to VPA in the 6 Hz 44 mA test.

Generally, in the 6 Hz model there is a significant decrease in the potency of antiepileptic drugs as the stimulation intensity is increased and in fact, all the old and new antiepileptic drugs tested in these models lost their efficacy in the 44 mA stimulus except high doses of levetiracetam ($ED_{50}$ 189 mg/kg) and Valproic Acid ($ED_{50}$ 310 mg/kg). The efficacy of compound 1 at the 3 tested stimulus intensities in the 6 Hz model and the negligible increase in its $ED_{50}$ value with increasing stimulus intensity distinguishes this compound from most other existing antiepileptic drugs.

Compound V of the above diagram (2-hydroxyethyl-tetramethylcyclopropane-carboxamide) was screened for its ability to protect against induced convulsions in MES and scMet test. Compound V was found to be active in mice at the MES and sc Met tests; 1 out of 4 mice was protected at the MES (maximal electroshock) test following a dose of 30 mg/kg ip. At the sc Met (subcutaneous metrazole) test, 3 out of 4 mice were protected following ip administration of 50 mg/kg.

2-hydroxyethyl-tetramethylcyclopropane-carboxamide did not show any behavioral impairment (or was not neurotoxic) at a does of 50 mg/kg ip.

EXAMPLE 4

Neurotoxicity

Neurotoxicity of the claimed agents was assessed in mice (ip. administration) in the rotorod ataxia test. Compound 1 was neurotoxic in some of the mice tested at doses of above 146 mg/kg ip. The PI for compound 1 at the highest stimulus intensity (44 mA) in the 6 Hz test in mice was 1.1 compared to 0.91 for VPA. This shows that compound 1 at this test has a wider safety of margin.

TABLE 1

Anticonvulsant activity ($ED_{50}$) and neurotoxicity ($TD_{50}$) obtained 15 min following ip administration of N-hydroxymethyl-tetramethylcyclopropane carboxamide to mice in comparison to VPA.

|  | Compound 1 | VPA |
|---|---|---|
| MES $ED_{50}$ (mg/kg) | 150–300 | 271 |
| sc Met $ED_{50}$ (mg/kg) | 120 | 149 |
| 6 Hz 22 mA (mg/kg) | 75 | 42 |
| 6 Hz 32 mA (mg/kg) | 91 | 126 |
| 6 Hz 44 mA (mg/kg) | 134 | 310 |
| Neurotoxicity $TD_{50}$ (mg/kg) | 146 | 283 |
| PI (6 Hz 44 mA) | 1.1 | 0.91 |

What is claimed is:

1. N-Hydroxyalkyl-tetramethylcyclopropane carboxamide derivative compound having the formula [I]:

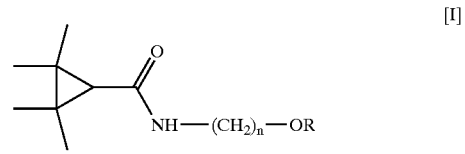

wherein n=1–6;
and R is hydrogen, an alkyl group of 1–3 carbons, an arylalkyl group, an aryl group, a carboxamide or N-Methyl or N-dimethyl carboxamide.

2. A pharmaceutical composition comprising an effective amount of the compound as defined in claim 1 as an active ingredient and a pharmaceutically acceptable carrier.

3. A pharmaceutical composition according to claim 2 wherein the effective amount is an amount from 10 to about 500 mg.

4. A pharmaceutical composition according to claim 2, wherein the carrier is a solid and the composition is in the form of a tablet.

5. A pharmaceutical composition according to claim 2, wherein the carrier is selected from the group consisting of an oil, a fat, a wax, a synthetic triglyceride and a polymer and the composition is a suppository.

6. A pharmaceutical composition according to claim 2, wherein the carrier is a liquid and the composition is in the form of a solution.

7. A pharmaceutical composition for the treatment of at least one of affective illness, cognitive disorders, neurodegenerative diseases, neurological disorders, psychotic disorders, neuropathic pain, chronic pain, headaches, migraines, epilepsy, bipolar disorders, stroke, brain ischemia and head trauma injury comprising as an active ingredient an effective amount for said treatment of N-Hydroxyalkyl-tetramethylcyclopropane carboxamide derivative according to formula [I] of claim 1 and a pharmaceutically acceptable carrier or diluent.

8. A method for treating a disease, disorder or condition selected from the group consisting of affective illness, cognitive disorders, neurodegenerative diseases, neurological disorders, psychotic disorders, neuropathic pain, chronic pain, headaches, migraines, epilepsy, bipolar disorders, stroke, brain ischemia and head trauma injury in a mammal in need of such treatment comprising administering to the mammal an effective amount of the compound as defined in claim 1.

\* \* \* \* \*